United States Patent
Smith et al.

(10) Patent No.: US 10,105,143 B2
(45) Date of Patent: Oct. 23, 2018

(54) CAP WITH BAND DEPLOYMENT FEATURES

(71) Applicant: Boston Scientific Scimed, Inc., Maple Grove, MN (US)

(72) Inventors: Paul Smith, Smithfield, RI (US); Andrew Schaubhut, Somerville, MA (US); Oscar R. Carrillo, Jr., Attleboro, MA (US); John B. Golden, Norton, MA (US); Brad M. Isaacson, Lancaster, MA (US); Michael D. Amos, Ayer, MA (US); Norman C. May, Northborough, MA (US); Dengzhu Yan, Marlborough, MA (US); James Weldon, Newton, MA (US); Daniel Congdon, Wenham, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 170 days.

(21) Appl. No.: 14/295,893

(22) Filed: Jun. 4, 2014

(65) Prior Publication Data

US 2014/0364873 A1    Dec. 11, 2014

Related U.S. Application Data

(60) Provisional application No. 61/831,331, filed on Jun. 5, 2013.

(51) Int. Cl.
*A61B 17/10* (2006.01)
*A61B 17/12* (2006.01)
(Continued)

(52) U.S. Cl.
CPC ...... *A61B 17/12013* (2013.01); *A61B 90/361* (2016.02); *A61B 2017/00269* (2013.01);
(Continued)

(58) Field of Classification Search
CPC .... A61B 2017/00296; A61B 17/12009; A61B 2017/12018; A61B 17/12013
See application file for complete search history.

(56) References Cited

U.S. PATENT DOCUMENTS 5,913,865 A * 6/1999 Fortier ............. A61B 17/12013
606/140
2003/0229359 A1    12/2003 Fortier et al.
(Continued)

FOREIGN PATENT DOCUMENTS

JP        2005515282        5/2002

OTHER PUBLICATIONS

International Search Report and Written Opinion for corresponding PCT Application No. PCT/US2014/040888, dated Sep. 22, 2014 (10 pages).
(Continued)

*Primary Examiner* — Kathleen Holwerda
*Assistant Examiner* — Christina Lauer
(74) *Attorney, Agent, or Firm* — Fay Kaplun & Marcin, LLP

(57) ABSTRACT

According to an embodiment of the present disclosure, a medical device for deploying a ligation band may include a tubular body. The tubular body may include a proximal end, a distal end, a radially inner surface defining a lumen through the tubular body, and a radially outer surface. The radially outer surface may include protrusions arranged in rows extending at least partially around a proximal region of the radially outer surface. Protrusions in adjacent rows may be separated by a first distance. Surface features may extend at least partially around a distal region of the radially outer surface. Adjacent surface features may be separated by a second distance larger than the first distance.

17 Claims, 12 Drawing Sheets

(51) Int. Cl.
*A61B 17/00* (2006.01)
*A61B 17/30* (2006.01)
*A61B 90/00* (2016.01)

(52) U.S. Cl.
CPC ............... *A61B 2017/00296* (2013.01); *A61B 2017/12018* (2013.01); *A61B 2017/306* (2013.01)

(56) References Cited

U.S. PATENT DOCUMENTS

2006/0129167 A1* 6/2006 Fortier ............. A61B 17/12013 606/140
2008/0097478 A1* 4/2008 Doughty .......... A61B 17/12013 606/140

OTHER PUBLICATIONS

Cannon, A. H., and King, W. P. "Hydrophobicity of Curved Microstructured Surfaces." J. Micromech. Microeng. 20 (2010) (6 pages).
Lee, Jae Bong, et al. "Wetting Transition Characteristics on Microstructured Hydrophobic Surfaces." Materials Transactions. vol. 51, No. 9 (2010), pp. 1709-1711.
Bhushan, Bharat. "Nature's Nanotechnology." Mechanical Engineering, vol. 34, No. 12, Dec. 2012 (6 pages).

* cited by examiner

CAP WITH BAND DEPLOYMENT FEATURES

CROSS-REFERENCE TO RELATED APPLICATIONS

This application claims the benefit of priority from U.S. Provisional Patent Application No. 61/831,331, filed on Jun. 5, 2013, the entirety of which is incorporated by reference herein.

FIELD OF THE DISCLOSURE

This disclosure relates generally to medical devices. More particularly, the disclosure relates to use of a cap for deploying bands. The cap and bands may be used for endoscopic mucosal resection (EMR) procedures.

BACKGROUND OF THE DISCLOSURE

Cancerous or benign lesions of the gastro-intestinal (GI) tract often start in the mucosal layer of the stomach or intestines. With improved diagnostics and screening, such lesions are generally identified before they affect the stomach and/or the intestines. Treatments and therapies for treating lesions have involved invasive surgical resection of the affected tissue or lesion. Early identification and treatment of such lesions, through methods including local excision of the mucosa, accessed via natural orifices, may be preferred as they are less invasive.

An example of a less invasive technique for treating tissue defects or lesions, including conditions related to varices, chronic liver disease, hemorrhoids, and the like, is band ligation. In band ligation, the affected or target tissue is bound with a band to form a pseudo polyp, thus establishing a ligated tissue. The ligated tissue may be removed using a removal device, such as a snare.

For band ligation, the band is delivered into the body as part of a ligation unit or device, which is configured to be steered and positioned adjacent the target tissue. Typically, ligation units are inserted into natural body cavities or through an incision, at a distal end of an endoscope.

In some ligation units, ligation bands may be tightly arranged over a cap-like structure, and deployed over the target tissue. Strings or sutures may be employed to advance the bands towards a distal end of the device to release the bands from the ligation unit. In some cases, portions of the band may slide along the surface of the cap, instead of rolling along the surface of the cap. Such a situation may lead to a twisted, angular, inverted, and/or otherwise undesirable deployment of the band, causing the tissue to be held improperly. For example, the band may fail to compress the tissue appropriately when deployed, causing the formation of a necked or otherwise misshaped polyp, or causing an increase in the risk of perforating underlying tissue layers.

To address such conditions, surface features can be provided on the cap-like structure to engage the bands during their deployment. Such surface features may, however, limit visibility through and around the cap-like structure, depending on their characteristics.

SUMMARY OF THE DISCLOSURE

The present disclosure describes a medical device for ligating a portion of tissue in a patient's body.

According to an embodiment of the present disclosure, a medical device for deploying a ligation band may include a tubular body. The tubular body may include a proximal end, a distal end, a radially inner surface defining a lumen through the tubular body, and a radially outer surface. The radially outer surface may include protrusions arranged in rows extending at least partially around a proximal region of the radially outer surface. Protrusions in adjacent rows may be separated by a first distance. Surface features may extend at least partially around a distal region of the radially outer surface. Adjacent surface features may be separated by a second distance larger than the first distance.

According to another embodiment of the present disclosure, a medical device for deploying a ligation band may include a tubular body. The tubular body may include a proximal end, a distal end, and a radially inner surface defining a lumen through the tubular body. The radially inner surface may include at least one radially inwardly extending protrusion configured to engage an imaging device. A proximal region of the tubular body may be proximal to the at least one radially inwardly extending protrusion, and a distal region of the tubular body may be distal to the at least one radially inwardly extending protrusion. The tubular body may also include a radially outer surface. The radially outer surface may include protrusions arranged in circumferentially extending rows on the radially outer surface, in the proximal region of the tubular body. Adjacent rows may be separated by a first distance. The radially outer surface may also include grooves extending circumferentially on the radially outer surface, in the distal region of the tubular body. Adjacent grooves may be separated by a second distance larger than the first distance.

According to another embodiment of the present disclosure, a medical device for deploying a ligation band may include a tubular body. The tubular body may include a proximal end, a distal end, a radially inner surface defining a lumen through the tubular body, and a radially outer surface. The radially outer surface may include a distal region, a proximal region, and a plurality of radially inwardly extending grooves formed in the radially outer surface, in the proximal region.

Additional objects and advantages of the described embodiments will be set forth in part in the description that follows, and in part will be apparent from the description, or, may be learned by practicing the disclosure. The objects and/or advantages of the disclosure will be realized and attained by way of the elements and combinations particularly pointed out in the appended claims.

It is to be understood that both the foregoing general description and the following detailed description are exemplary and explanatory only, and are not restrictive of the described embodiments, as claimed.

BRIEF DESCRIPTION OF THE DRAWINGS

The accompanying drawings, which are incorporated in and constitute a part of this specification, illustrate exemplary embodiments of the present disclosure, and together with the description, serve to explain the principles of the disclosure.

DESCRIPTION OF THE EMBODIMENTS

Reference will now be made to embodiments of the present disclosure, examples of which are illustrated in the accompanying drawings. Wherever possible, the same reference numbers will be used throughout the drawings to refer to the same or like parts. The term "distal" refers to the end farthest away from a medical professional when introducing a device in a patient. The term "proximal" refers to the end closest to the medical professional when placing a device in the patient.

Overview

Embodiments of the present disclosure relate to devices configured for ligating tissue. For example, embodiments of the disclosed device may facilitate ligation of infectious, dead, or otherwise undesired tissue, which may form conditions such as hemorrhoids, mucositis, early gastrointestinal cancer, lesions, or varices, and/or may include undesired patches of tissue disposed on, for example, the mucosal walls of the colon, esophagus, stomach, or duodenum.

In some embodiments, a medical device may include a cap configured for attachment to a distal end of a sheath or a suitable elongate device, such as a catheter shaft, endoscope, laparoscope, colonoscope, ureteroscope, or the like. The cap may include an outer surface, a proximal end, a distal end, and a cavity extending through the cap, between those ends. The cavity may be open at its proximal and distal ends. One or more bands may be disposed on a proximal end portion of the cap, over the outer surface. The outer surface may include one or more band deployment features between the proximal and distal ends of the cap. The one or more band deployment features may provide for a regulated or controlled rolling motion of the bands, and subsequent release of the bands from the cap. A suture may be coupled to the bands to pull the bands along the cap, and release the bands from the cap, one at a time, from the distal end of the cap onto tissue.

Exemplary Embodiments

The cap embodiments disclosed herein may be employed along with an elongate device, which may include an endoscope, to introduce and deliver the caps to a target site within a patient's body. It is contemplated, however, that the present disclosure may be used along with other introduction devices, sheaths, or systems, such as trocars, catheter sheaths, laparoscopes, colonoscopes, ureteroscopes, or the like.

Figure 1A:
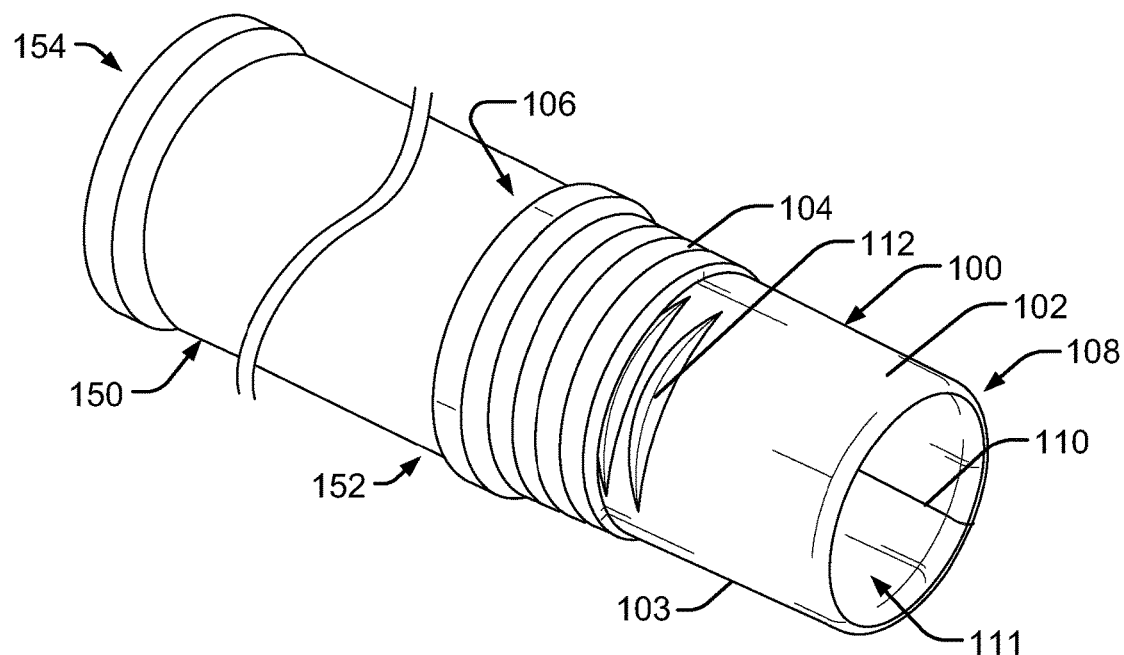
FIG. 1A is an isometric view of an exemplary ligation cap affixed to a distal end of a sheath, such as an endoscope, according to aspects of the present disclosure.

FIG. 1A is an exemplary ligation cap 100, configured to be secured to a distal end 152 of an endoscope 150. The cap 100 may include a tubular body, and may include an outer surface 102. One or more ligation bands 104 may be positioned around a proximal end portion 106 of the cap 100. Seven bands 104 may be accommodated around the outer surface 102, but it should be understood that fewer or more bands 104 may be used depending on the type of procedure being performed. Towards the distal end portion 108 of the cap, a suture 110 that extends through a cavity 111 of the cap 100, may be disposed. The suture 110 may be configured to pull at least one of the bands 104, facilitating releasing of each of the bands 104 from the distal end portion 108 of the cap 100. Over the outer surface 102, grooves 112 may be disposed. The suture 110 may extend over one side of the outer surface 102, and the grooves 112 may be disposed on an opposite side of the outer surface 102.

The cap 100, and the other ligation caps disclosed herein, may be configured to be permanently or temporarily secured to the distal end 152 of the endoscope 150, via suitable securing mechanisms. Permanent securing mechanisms may include, for example, adhesives, welding, soldering, or the like, while temporary securing mechanisms may include snap-fit, screw-fit, luer-lock, or the like. In some instances, the cap 100 may be integral with the endoscope 150.

Further, the cap 100 may be application specific, and may be relatively small enough for being appropriately inserted and navigated to reach a target site through natural body cavities or through an incision. For example, external dimensions of the cap 100 may vary from application to application. For example, if the cap 100 is anally inserted to resect internal hemorrhoids, the dimensions of the cap 100 may be considerably smaller than a similar device used in connection with treating esophageal varices. Understandably, the shape and size of a corresponding endoscope may vary as well. A plurality of differently sized or configured caps may be provided in a kit, allowing a user to select a cap from the kit based on the type of procedure to be performed.

Additionally, the cap 100 may be designed for multiple or single use applications. For single-use applications, for example, the cap 100 may have a temporary attachment mechanism, such as a screw-fit, and may thus be stored and disposed of in hermetically sealed and sterile packaging. On the other hand, a multiple-use device may be adapted to be sterilized, and thus, may be designed with materials able to withstand extreme temperature, chemical reactions, pressure variations, etc. For enabling a multiple use, the cap 100 may be made from high grade materials that are compliant to be fixed and removed regularly, such that a repeated use is possible. Furthermore, a multiple use cap 100 may also be permanently affixed to the endoscope 150, and may be sterilized along with the endoscope 150 for repeated applications.

At the distal end portion 108, the cap 100 may be rounded off or chamfered to facilitate band deployment. A rounded off or chamfered edge 126 at the distal end portion 108 may also make the cap 100 atraumatic, reducing likelihood of tissue damage when coming in contact with tissue during its travel to a target site.

In some embodiments, the cap 100 may be made from a transparent or a semi-transparent material, such that visualization through the cap 100 by an operator or a surgeon is possible. For example, the distal end 152 of the endoscope 150 may have an imaging device, such as a sensor or camera with a lens (not shown), positioned therein. For example, the imaging device may be inserted through the endoscope 150 from a proximal end portion of the endoscope 150. The imaging device may be inserted through the endoscope 150 to a position near a proximal end portion 106 of the cap 100. It is also contemplated that the imaging device and/or the distal end 152 of the endoscope may be inserted past the proximal end portion 106 of the cap 100 to a stop (described in more detail below), and positioned within the cavity 111 of the cap 100. The field of view of the imaging device may include regions visible to the imaging device beyond the distal end portion 108 of the cap 100, and regions visible to the imaging device peripherally through side walls of the cap 100.

The cavity 111 may be a substantially cylindrical lumen, communicating with a lumen (not shown in FIG. 1A, but shown in FIG. 8) of the endoscope 150, at the cap's proximal end portion 106. Surfaces of the cap 100 that form the cavity 111 may be substantially smooth and flat. The cavity 111, at the proximal end portion 106, may be dimensioned to fit over or mate with the distal end 152 of the endoscope 150. Shapes and dimensions of the cavity 111 and the endoscope 150 may correspond to each other by, for example, being complementary, enabling the cavity 111 to be operably assembled flush to the lumen (not shown) structured within the endoscope 150.

Figure 10A:
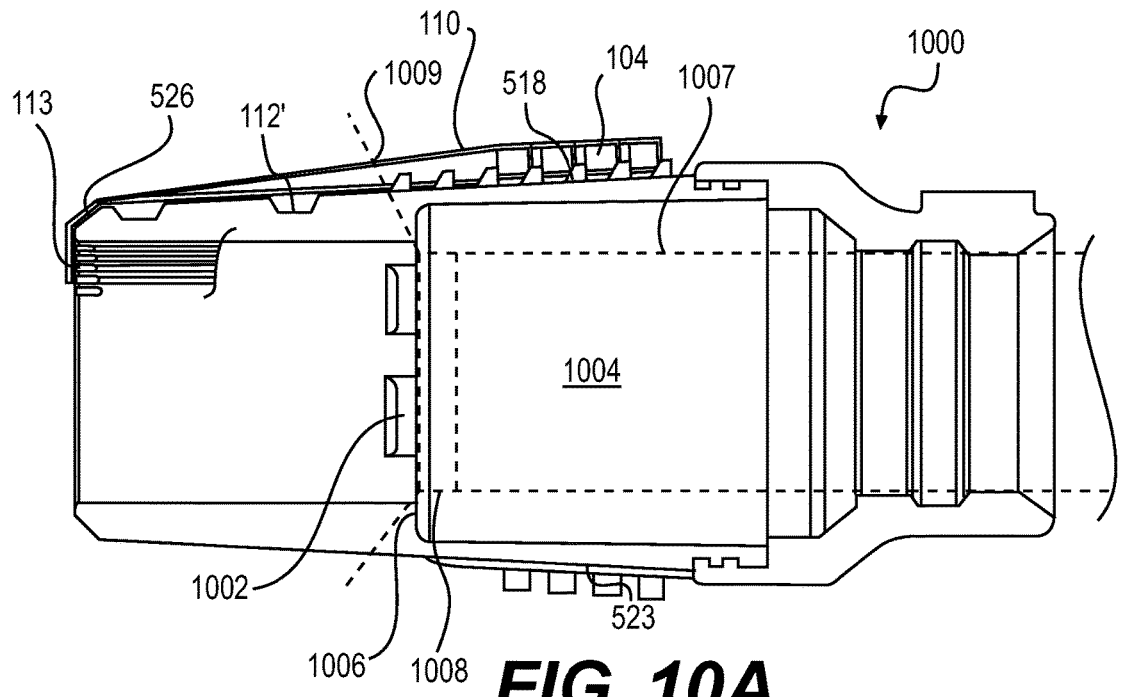
FIGS. 10A-10C are perspective views of alternative embodiments of a cap, according to aspects of the present disclosure.

It is also contemplated that surfaces of the cap 100 that form the cavity 111 may include a step (not shown) similar to a step 1006 shown in FIG. 10A, dividing the cavity 111 into a larger diameter proximal portion and a smaller diameter distal portion. Additionally or alternatively, surfaces of the cap 100 that form the cavity 111 may include one or more protrusions (not shown), extending radially inward from the surfaces, similar to one or more protrusions 1002 shown in FIG. 10A. The one or more protrusions may abut a structure on the endoscope 152, such as the distal end 152 of the endoscope 150, and/or a structure on the imaging device, acting as a stop to help a user position the endoscope 150 and/or imaging device relative to the cap 100 in a consistent and repeatable manner. For example, the one or more protrusions may abut the imaging device such that the grooves 112, and/or bands 104 engaging the grooves 112, may be outside of (e.g., proximal to) the field of view of the imaging device. The grooves 112 and/or bands 104 thereon may be outside of the field of view even if portions of the grooves 112 and/or bands 104 thereon may be distal to the imaging device.

Figure 1B:
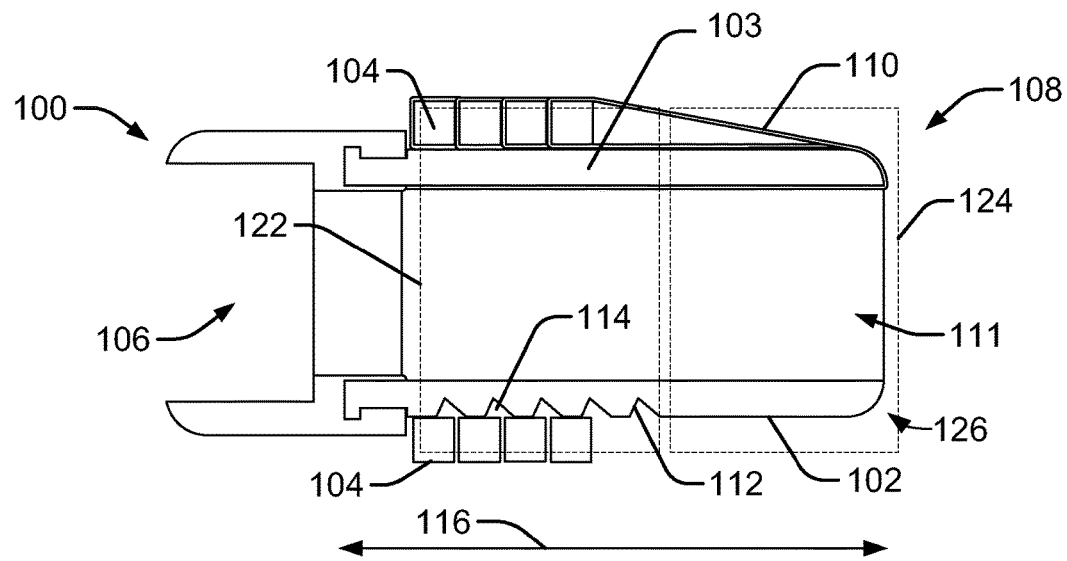
FIG. 1B is a cross-sectional side view of the cap of FIG. 1A.

At the distal end portion 108 of the cap 100, the suture 110 may extend distally within the cavity 111, bend around the distal end portion 108 of the cap 100, and extend proximally to the bands 104. At least a portion of the suture 110 may extend proximally through the endoscope 150. A proximal portion of the suture 110 may extend proximally out from a proximal end 154 of the endoscope 150, all the way till the distal end portion 108 of the cap 100. While in operation, a predetermined proximal pull on the suture 110 may deploy one band 104 at a time from the cap 100. FIG. 1B depicts the suture 110 being wrapped around the bands 104 disposed on the outer surface 102 of the cap 100.

The suture 110 may wrap over each band 104 in a sequential fashion. In detail, beyond a first wrap, the suture 110 may extend back and bend over the edge 126, before extending forth and being wrapped over the next band 104. Similarly, all the bands 104 may be sequentially wrapped by a single suture 110. In such an instance, a first proximal pull on the band 104 would facilitate pulling a first band 104 towards the distal end portion 108 of the cap 100, for eventual release onto tissue. For releasing the second, third, and subsequent ligations bands 104, the suture 110 may be pulled a second, a third, and subsequent times. Further description of the suture 110 and bands 104, their operation, and possible alternative arrangements, are described in U.S. Pat. No. 5,913,865, which is incorporated herein by reference in its entirety.

The bands 104 disposed over the outer surface 102 may be resilient, formed of a material such as rubber. The bands 104 may be configured to roll over at least a portion of the outer surface 102, when engaged by grooves 112. The bands 104 are substantially ring-shaped elastic structures similar to rubber bands, and are configured to constrict and ligate tissue. Generally, the bands 104 may have a square cross-section that promotes turning or rolling of the band 104 over the outer surface 102. Other cross-sectional profiles of the band 104 may be envisioned as well, and those may include rectangular, triangular, hexagonal, round, elliptical, irregular, and other suitable profiles.

The outer surface 102 may include two regions. A first region 122 (see FIG. 1B) may include deployment features, such as the grooves 112, facilitating the rolling of the bands 104 over the outer surface 102, instead of facilitating pure sliding of the bands 104 over the outer surface 102. The grooves 112 may be disposed at least partially around the outer surface 102. Further, the grooves 112 may extend only partially around a circumference of the outer surface 102 to help ensure that grooves 112 minimally obstruct a field of view of the imaging device. The grooves 112 may be widest at their centers, and may become thinner towards their ends. The widths of the grooves 112 may approach zero at their ends, forming pointed groove ends. The grooves 112 may be deepest at their centers, and may become shallower towards their ends. The depths of the grooves 112 may approach zero at their ends. The lengths, width features, and depth features of the grooves 112 may be configured to reduce obstructions to visibility through the cap 100 from the perspective of the imaging device (not shown), and the user viewing images sent by the imaging device. For example, the surfaces of the deployment features (e.g. grooves 112, spikes or protrusions 218, 518) may be angled or positioned relevant to the imaging device to minimize any obstruction or distortion to the image detected by the imaging device. This may be achieved by aligning the planar surface of a deployment feature with the line of sight (i.e. sightline or visual axis) of the imaging device. The lengths, width features, and depth features of the grooves 112 may also be configured to generate forces on or in certain parts of the bands 104 at certain moments during deployment of the bands 104, while not generating forces on or in other parts of the bands 104 at those moments. This selective generation of forces on the bands 104 may facilitate their rolling deployment.

Certain embodiments may include fewer or more of the grooves 112 than the number shown. Additionally, shapes, sizes and positioning of the grooves 112 may vary from that which is depicted. Moreover, an amount of spacing between each of the grooves within the set of grooves 112 may vary.

The grooves 112 may extend part of the way along the outer surface's longitudinal length 116, beyond which a second region 124 may extend to the distal end portion 108 of the cap 100. Such a placement of the set of grooves 112 may vary, with the set of grooves 112 ending either before, at, or after the halfway mark along the longitudinal length 116. The second region 124 may be free of grooves 112.

The first region 122 or the second region 124 may optionally include a tapered profile in which an outer diameter of the region decreases toward the distal end portion 108. In some embodiments, the entire outer surface 102, structured over both the regions 122 and 124, may taper along the longitudinal length 116, to the distal end portion 108. The tapering profile of the cap 100 may encourage movement of the bands 104 toward the distal end portion 108.

FIG. 1B depicts a cross-sectional view of the cap 100 illustrating a side profile of the grooves 112 disposed along the outer surface's longitudinal length 116. A triangular cross-sectional profile 114 of the grooves 112 is shown, where a leading/proximal surface of the groove 112 may incline more than a following/distal surface. Portions of the bands 104 may contact the outer surface 102 of the cap 100, while other portions of the bands 104 may extend over the grooves 112. As such, the grooves 112 may reduce surface contact and/or friction between the bands 104 and the outer surface 102 of the cap 100.

The grooves 112 may receive portions of the bands 104 as they move along the outer surface 102. For example, proximal and distal edges of the grooves 112 may act as teetering points for the bands 104. The bands 104 may teeter on the edges of the grooves 112, tilt, and then rotate into the grooves 112. For example, corner portions of the bands 104 may tilt and then rotate into and out of the grooves 112 as the bands 104 move distally along the cap 100. The reduced surface contact between the bands 104 and the outer surface 102, and/or the presence of teetering points for the bands 104, may encourage rolling of the bands 104 as they move distally along outer surface 102. Other embodiments of the grooves 112 may be envisioned as well, and the forthcoming description includes discussion related to those embodiments.

Figure 2A:
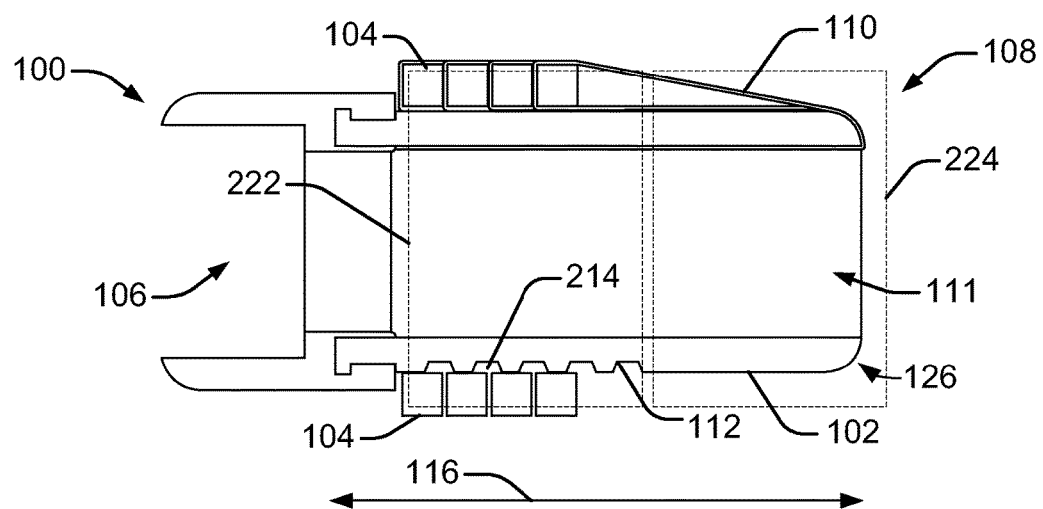
FIGS. 2A, 2B, and 2C, are cross-sectional side views depicting alternative embodiments of the cap, according to aspects of the present disclosure.
Figure 2B:
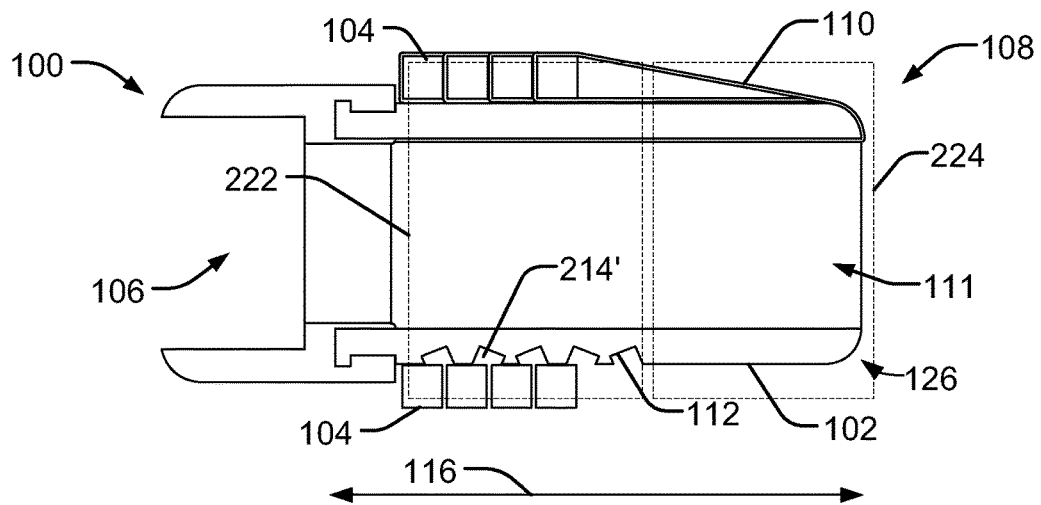
Figure 2C:
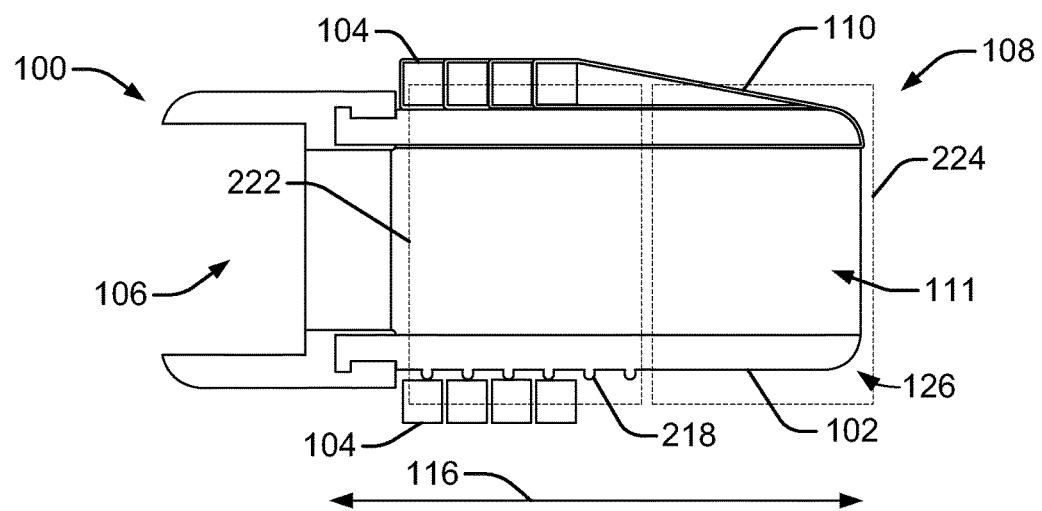

Accordingly, embodiments of the cap 100 depicted in FIGS. 2A, 2B, and 2C, include alternate forms of the grooves 112 disposed within a corresponding first region 222. More specifically, FIG. 2A illustrates the cap 100 with a set of grooves 112 having a trapezoidal profile 214, while FIG. 2B depicts a cap 100 having a profile 214' with sharp points or edges for engaging the bands 104. Some embodiments may include, but are not limited to, rectangular and/or irregular cross-sectional profiles. As described above, the grooves 112 may reduce surface contact between the bands 104 and the outer surface 102, and/or provide teetering points for the bands 104 (e.g., at edges of the grooves 112), to encourage tilting and then rolling of the bands 104 as they move distally along the outer surface 102.

Optionally, the set of grooves 112 may be replaced by or augmented with spikes, other protrusions, their combinations, and the like. Accordingly, FIG. 2C depicts a cross-sectional profile of the cap 100, having a set of spikes or protrusions 218, in place of the set of grooves 112, disposed over the outer surface 102. The protrusions 218 may initiate rolling of the bands 104. The protrusions 218 may reduce surface contact between the bands 104 and the outer surface 102, since only portions of the radially-inner surfaces of the bands 104 will contact the outer surface 102. The protrusions 218 may act as teetering points for the bands 104. For example, peaks of the protrusions 218 may act as teetering points for the bands 104. As the bands 104 come into contact with the protrusions 218, the teetering points may encourage tilting and rotating of portions of the bands 104, into and out of gaps between the protrusions 218. The reduced surface contact and/or teetering points may encourage rolling of bands 104 as they move distally along the outer surface 102.

As discussed above, the grooves 112 and all its embodiments, when applied, may be transparent, or at least semi-transparent, enabling light to pass through those areas. Such a feature may enable an environment disposed beyond and around the distal end portion 108 of the cap 100 to be visible from within the cavity 111, from the perspective of an imaging device (not shown) at or near the distal end 152 of the endoscope 150.

Other embodiments of the frictional surface or the set of grooves 112 are also contemplated. For example, the grooves 112, or the spikes or protrusions 218, may be provided at an angle over the outer surface 102. In some embodiments, a rubberized layer disposed over the outer surface 102 may provide a requisite amount of friction or traction to initiate and sustain the rolling motion of the bands 104 during deployment. Such employment of a rubberized grip may prove economical and easy to manufacture, while being equally efficient as well. Another embodiment may include the outer surface 102 being made or covered by the same material as the bands 104.

Figure 3A:
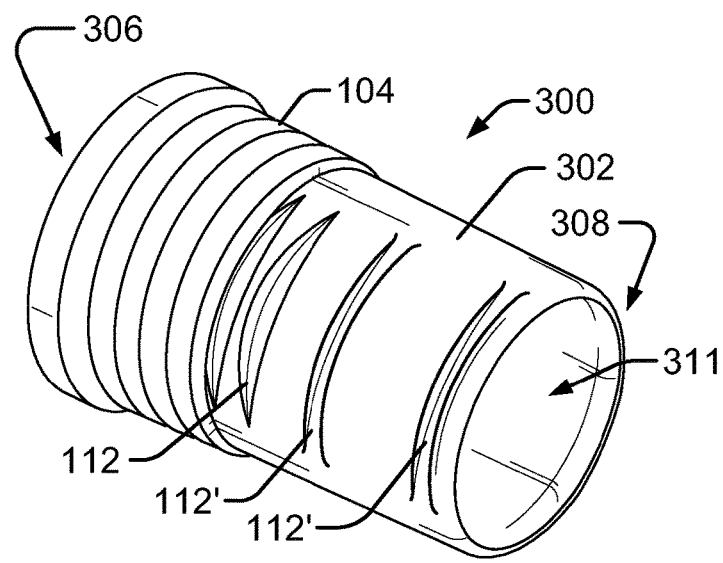
FIG. 3A is an isometric view of an embodiment of a cap, according to aspects of the present disclosure.

FIG. 3A illustrates an exemplary cap 300, with the outer surface 302 having two regions, similar to the ones discussed above. Here, while the rest of the structure of the cap 300 may remain substantially similar, a corresponding outer surface 302 may include a first set of grooves 112 positioned at a proximal end portion 306, and a second set of grooves 112' positioned closer to a distal end portion 308 of the cap 300. If the bands 104 begin to slide or slip, the grooves 112' may engage the bands 104 to provide a correction factor and reduce strain in the bands 104, and/or to encourage further rolling of the bands 104. Further, because the grooves 112' are cut into the cap 300, they also help to minimize band strain during deployment, and the amount of force needed to move the bands during deployment. It is contemplated that grooves 112', similar to grooves 112, may provide teetering points (e.g., at edges of grooves 112') for bands 104, to encourage teetering, tilting, and rolling of the bands 104 as they move distally along the outer surface 302.

Figure 3B:
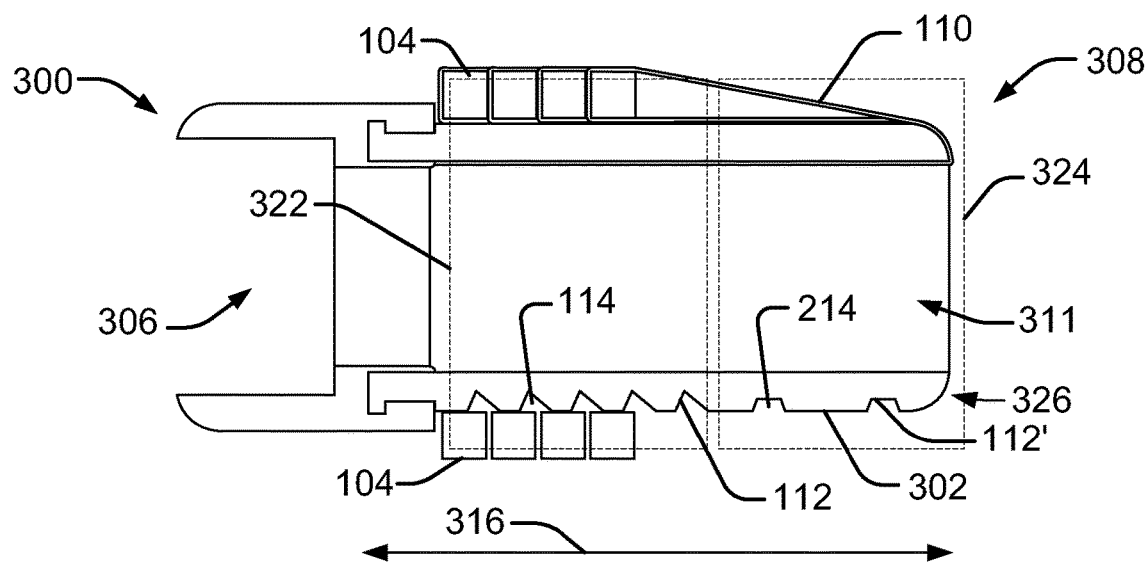
FIG. 3B is a cross-sectional side view of the cap of FIG. 3A, according to aspects of the present disclosure.

FIG. 3B illustrates a side cross-sectional view of the cap 300, depicting the two regions, which are marked as a first region 322, and a second region 324. Notably, the two regions 322 and 324 may include differently configured set of grooves 112 and 112'. For example, the set of grooves 112 may include a triangular cross-sectional profile 114, while the set of grooves 112' may include a rectangular or a trapezoidal cross-sectional profile 214.

It is also contemplated that the spacing between the most distal groove 112', and the distal end portion 308 of the cap 300, may be less than the minimum distance traveled by the band 104 during the band's 360° rolling motion. Such a structure may enable the band's release from the cap 300, when travelling beyond the distal most groove 112'. It is also contemplated that a space between adjacent grooves 112' may be greater than a space between adjacent grooves 112. Additionally or alternatively, there may be fewer grooves 112' than grooves 112. Such an arrangement may facilitate visualization at the distal end portion 308 of the cap 300 when viewing through the cavity 311 from the proximal end portion 306 of the cap 300, using the imaging device (not shown).

Relatively closely spaced set of grooves 112 in the first region 322 may facilitate or induce a rolling motion of the bands 104 towards the distal end portion 308. This is because pulling the bands 104 toward the distal end portion 308 may cause the bands 104 to at least partially enter into an adjacent groove disposed in the direction of the distal end portion 308. The pulling force may be generated by the suture 110. The second region 324 may also facilitate the rolling motion and exit of the bands 104 at the distal end portion 308 of the cap 300.

Figure 4A:
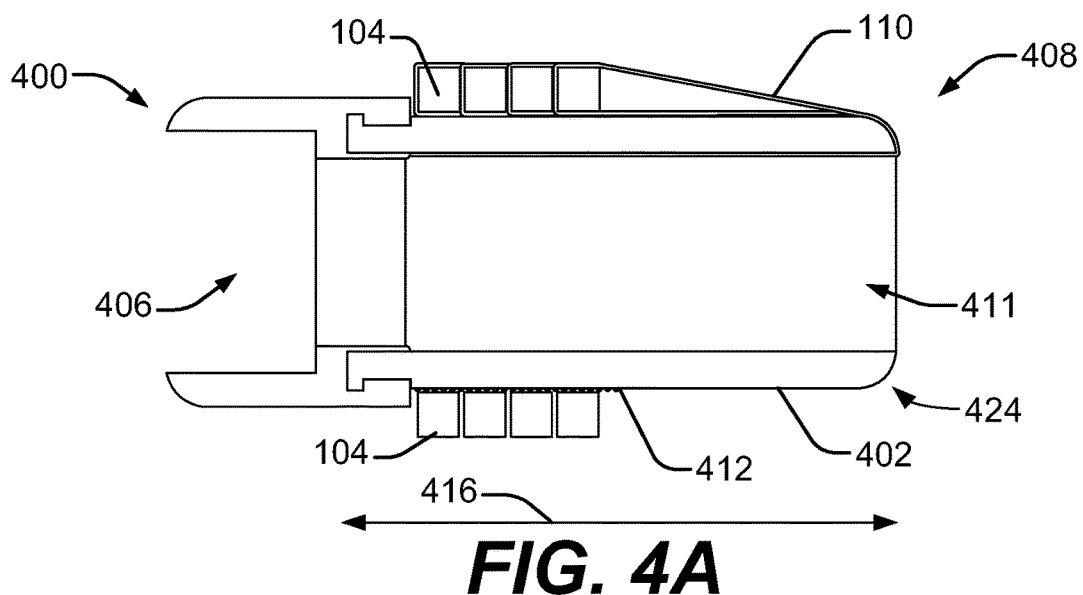
FIG. 4A is cross-sectional side view of another embodiment of a cap, according to aspects of the present disclosure.

FIG. 4A shows a cross-section of another embodiment of an exemplary cap 400 with an outer surface 402. Here, while the rest of the structure of the cap 400 may remain substantially similar, the outer surface 402 may include a pattern, such as a micropattern 412 composed of an array of microstructures 422. The micropattern 412 may extend along at least a portion of a longitudinal length 416 of the cap 400. The portion of the longitudinal length 416 may include a proximal portion or a distal portion. It is also contemplated that the micropattern 412 may extend along all of the longitudinal length 416. The micropattern 412 may be disposed circumferentially along at least a portion of a circumference of the outer surface 402. In one embodiment, the micropattern 412 may extend around an entire circumference of the outer surface 402. It is also contemplated that the micropattern 412 may be in the form of a circumferential band, a spiral or helix, an irregular or random form, and/or any other suitable form or combination of forms to help achieve a desired band deployment characteristic.

Figure 4B:
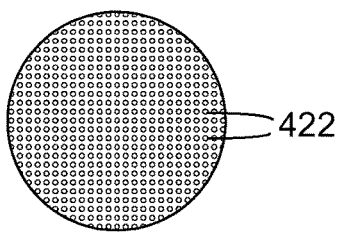
FIG. 4B is an enlarged view of microstructures, according to aspects of the present disclosure.
Figure 4C:
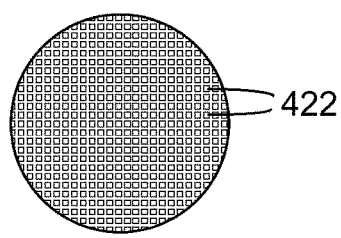
FIG. 4C is another enlarged view of microstructures, according to aspects of the present disclosure.

As depicted in FIGS. 4B and 4C, the micropattern 412 may include a plurality of microstructures 422 spaced apart from each other. In FIG. 4B, the microstructures 422 may include pillars or fibers (e.g., nanopillars or nanofibers) of circular cross-section, arranged in form of a matrix, with gaps between adjacent microstructures 422. In FIG. 4C, the microstructures 422 may include pillars or fibers (e.g., nanopillars or nanofibers) of square-shaped cross-section, arranged in a matrix, with a smaller gap between adjacent microstructures 422. The microstructures 422 may also have other cross-sections, such as rectangular, elliptical, triangular, or the like. While it is contemplated that the microstructures 422 may be arranged in a the form of a grid, it is also contemplated that the microstructures 422 may be arranged in a diagonal pattern, a staggered pattern, a random or irregular pattern, and/or any other suitable pattern or combination of patterns to achieve a desired band deployment characteristic.

The small scale of the microstructures 422 allow the microstructures 422 to be present on the outer surface 402 of the cap 400 with little effect on visibility through the cap 400 from the perspective of the imaging device (not shown). It is contemplated that the micropatterns 412 and microstructures 422 can be formed on the outer surface 402 by molding, overmolding, extruding, chemical-etching, or machining, such as skiving, compressing material between dies, laser etching, or making by any other suitable method.

Based on the density and/or dimensions of the microstructures 422, certain characteristics may be imparted to the material on which the microstructures 422 are applied. For example, applying a first micropattern of first microstructures having a first width, to a first portion of the outer surface 402, may cause an increase in the gripping force exerted by the first portion of the outer surface 402 on the band 104, due to the micropattern having a first microstructure density at least partially determined by the first width. Applying a second micropattern of second microstructures having a larger second width, to a second portion of the outer surface 402, may cause a decrease in the gripping force exerted by the second portion of the outer surface 402 on the band 104, due to the micropattern having a second microstructure density that is less than the first microstructure density, at least partially determined by the second width.

In some embodiments, the microstructures, and spaces between them, may be nanometer scale, or micrometer scale. For example, the microstructures and/or the spaces may have widths between approximately 100 nm and 500 micrometers. In one embodiment, the first microstructures may include nanofibers (e.g., carbon nanotubes sprayed onto a flat epoxy resin, or thin polypropylene fibers) having a diameter between 100 and 600 nm. The second microstructures may include similar nanofibers, but ones having a diameter between 5 and 14 micrometers. It is also contemplated that the first microstructures may include micropillars with a diameter of approximately 105 micrometers, a height of 150 micrometers, and spacing (between micropillars) of approximately 100 to 340 micrometers. Thus, the first microstructures may have a spacing-to-diameter ratio of approximately 0.952 to 3.238. The second microstructures may include micropillars with different diameters and/or spacing, and in particular, a spacing-to-diameter ratio greater than the spacing-to-diameter ratio for the first microstructures (e.g., greater than 3.238).

It is also contemplated that the microstructures may be compound structures. For example, the microstructures may include bristles, each around 30-130 micrometers long. The bristles may explode into a spray of 100 to 1,000 branches that form the points of contact with a surface, such as the surface of a band 104. The tip of each branch may flatten into a spatula only about 10 nm thick. Such an arrangement may increase the gripping forces between the microstructures and the band 104, allowing adhesion between the microstructures and the band 104 even when one or the other is wet.

By changing microstructure characteristics (e.g., size, shape, and/or composition), and/or by changing micropattern characteristics (e.g., size, pattern design, and/or microstructure spacing), the gripping force exerted by the microstructures and micropatterns may be adjusted up or down. Many combinations of the above characteristics may be employed to achieve one or more intended effects. Thus, the examples of microstructure and micropattern characteristics provided above are exemplary only, and not intended to be exhaustive or limiting.

One way the first micropattern may increase the gripping force is by making a first portion of the outer surface 402, on which the first micropattern is applied, more hydrophobic. That is, a fluid contacting the first portion may bead and roll off the first portion more easily than other portions of the outer surface 402 that do not have the first micropattern. This may reduce the amount of fluid on the first portion. By reducing the amount of fluid on the first portion, sliding of the bands 104 on the first portion, caused by wetting of the first portion, may be reduced. For hydrophobicity, microstructures and microstructure spacing may be selected such that droplets of water tend to stand on tips of the microstructures, such that the droplets may roll off the tips of the microstructures with little force.

The second micropattern may decrease the gripping force by making a second portion of the outer surface 402, on which the second micropattern is applied, less hydrophobic. That is, a fluid contacting the second portion may tend to spread on and wet the second portion more easily than on the first portion. This wetting may make increase the likelihood of sliding of the bands 104 on the second portion.

In some instances, depending on environment of use, applying a micropattern on the outer surface 402 to make the outer surface less hydrophobic, and more hydrophilic, may provide other benefits. For example, hydrophilic coatings may have reduced fouling or protein aggregation when in use. This is because proteins may slough off of hydrophilic coatings. By making the outer surface 402 more hydrophilic, long-term visibility through the cap 400 may be improved, since proteins would tend to slough off of the outer surface 402, instead of adhering to or building on the outer surface 402 and blocking or otherwise limiting visibility.

By applying the first micropattern to a distal portion of the outer surface 402, the gripping force of the distal portion may be enhanced, causing rolling of the bands 104 as they move along the distal portion of the outer surface 402. The first micropattern may be applied in the region of the cap 400 analogous to the regions 124, 224, or 324. It is also contemplated that the first micropattern may be applied to the regions 124, 224, or 324, including on the grooves 112'. In another embodiment, the first micropattern may be applied to a proximal portion of the outer surface 402, causing the gripping force of the proximal portion to be enhanced, allowing the proximal portion to cause rolling of the bands 104 in a manner similar to the grooves 112. For example, the first micropattern may be applied in the region of the cap 400 analogous to the regions 122, 222, or 322. It is also contemplated that the first micropattern may be applied to the regions 122, 222, or 322, including on the grooves 112, 214, 214', or 218.

The second micropattern may be applied to portions of the outer surface 402 in which gripping force should be reduced. For example, the second micropattern may be applied to portions of the outer surface on which the first micropattern has not been applied. It is also contemplated that the first and second micropatterns may be arranged in alternating bands along the length of the outer surface 402.

By controlling the gripping force using one or more micropatterns 412, the positioning of the bands 104 during deployment can be controlled. For example, rolling of a band 104 may be initiated for a first part of the band 104, at a certain time during deployment, by providing the first micropattern on a first region of the outer surface 402 engaging the first part of the band 104. Rolling of a second part of the band 104 may not be initiated at that time, for a second part of the band 104, by omitting the first micropattern or providing the second micropattern on a second region of the outer surface 402 engaging the second part of the band 104. Tilting of the band 104 due, for example, to one part of the band 104 lagging behind another part of the band 104, may also be controlled, by using one or more micropatterns 412 to speed up or slow down portions of the band 104 during deployment.

Figure 5A:
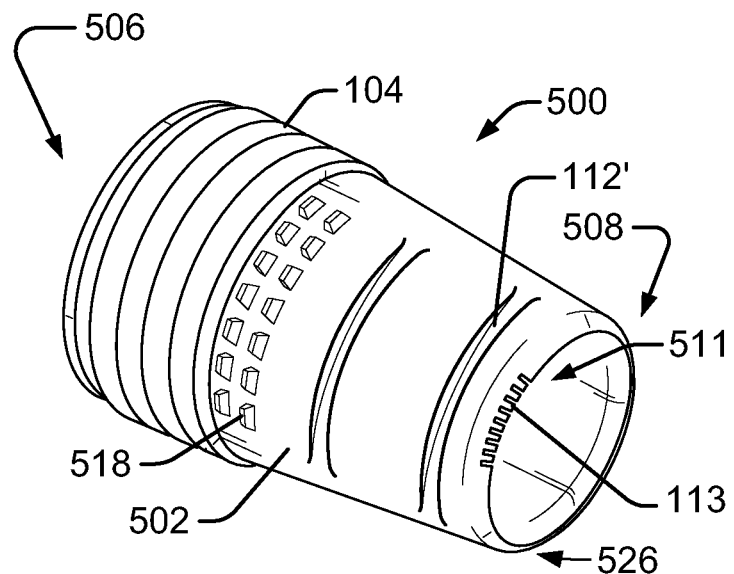
FIG. 5A is an isometric view of a cap, according to aspects of the present disclosure.
Figure 5B:
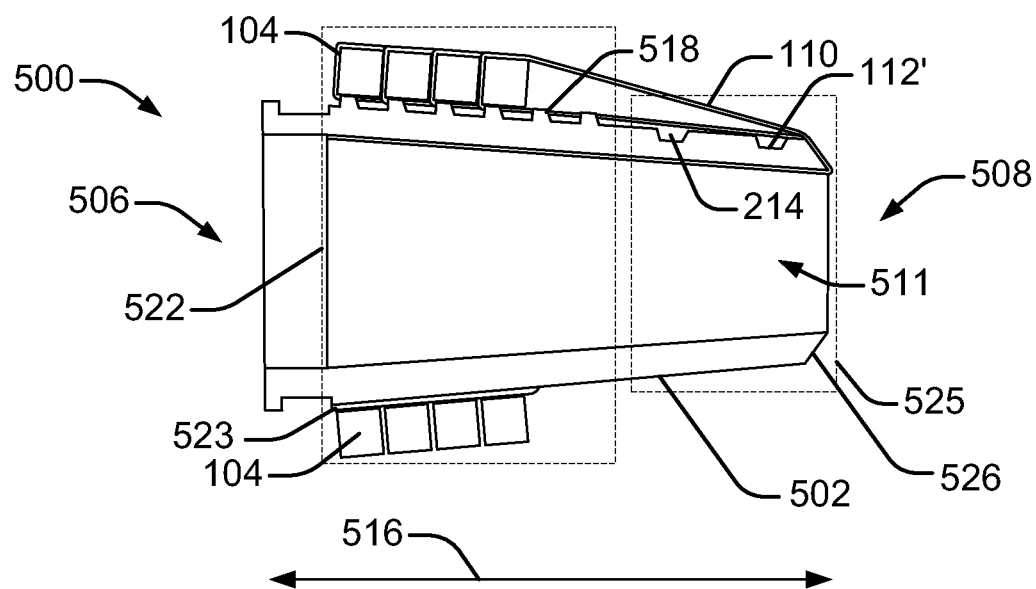
FIG. 5B is a cross-sectional side view of the cap of FIG. 5A, according to aspects of the present disclosure.

Additional embodiments of the present disclosure are shown in FIGS. 5A and 5B, which disclose a cap 500, with a first region 522 (see FIG. 5B) including protrusions 518, for initiating rolling of the bands 104, and a second region 525 (see FIG. 5B) including grooves 112'. Further, FIG. 5B illustrates a cross-sectional side view of the cap 500, where the set of protrusions 518 and set of grooves 112' are depicted over an outer surface 502 of the cap 500. A lumen 511, similar in form and function to cavity 111, may extend from the proximal end portion 506 to the distal end portion 508 of the cap 500. Alternatively, it is contemplated that the cross-sectional side view of the cap 500 may be similar to the cross-sectional side view of the cap 1000 shown in FIG. 10A.

Referring to FIGS. 5A and 10A, according to one aspect of the present disclosure, a first plane extending through a center of the distal groove 112', and perpendicular to a longitudinal axis of the cap, may lie approximately 0.350 inches from a parallel second plane extending through a proximal end of the one or more protrusions 1002. The first plane may be positioned approximately 0.100 inches from a distal end of the cap 1000, to help ensure that the bands 104 will not become jammed on the cap 1000 prior to deployment. A parallel third plane extending through a center of the proximal groove 112', may lie approximately 0.150 inches from the second plane. The spacing of the planes and grooves 112' encourages rolling of the bands 104, to help ensure that rolling deployment of the bands 104 may be achieved with minimal impact on visualization through the cap 500 via the imaging device (not shown). The second plane may be distal to the most distal row of the protrusions 518. Alternatively, the second plane may be proximal to the most distal row of the protrusions 518, but the second plane may be distal enough that the most distal row of the protrusions 518 may not obstruct a peripheral field of vision of an imaging device (not shown) in the cavity 511.

In one embodiment of the present disclosure, the grooves 112' may have a width of approximately 0.050 inches at their centers. In another embodiment of the present disclosure, the grooves 112' may have a width of approximately 0.070 inches at their centers. In one embodiment of the present disclosure, the grooves 112' may have a depth of approximately 0.020 inches at their centers, tapering off to a depth approaching zero at their ends. Edges of the grooves 112', such as proximal and/or distal edges of the grooves 112', may act as teetering points for bands 104. The reduced surface contact and/or teetering points may encourage teetering, tilting, and rolling of the bands 104 as they move distally along the outer surface 502.

Bands 104 may be positioned around a proximal end portion 506 of the cap 500, with inner surfaces of the bands 104 resting on outer surfaces of the protrusions 518. The protrusions 518 may be arranged in substantially parallel circumferentially extending rows, and/or in substantially parallel longitudinally extending columns. A suture 110 may lie in gaps between adjacent columns as the suture 110 extends proximally along the outer surface 502 and around the bands 104. The protrusions 518 may reduce surface contact between the bands 104 and the outer surface 502. Edges of the protrusions 518, such as the proximal and/or distal edges at their peaks, may act as teetering points for bands 104, encouraging portions of bands 104 to teeter, tilt, and rotate into and out of the gaps between the protrusions 518. The reduced surface contact and/or teetering points may encourage rolling of the bands 104 as they move distally along the outer surface 502.

At the distal end portion 108 of the cap 500, one or more slots or channels 113 (FIG. 5A) may be provided to guide portions of the suture 110 as the suture 110 extends distally within the cavity 511, bends around the distal end portion 508 of the cap 500, and extends proximally to the bands 104. At least a portion of the suture 110 may extend proximally through an endoscope, similar to the endoscope 150 (FIG. 1A).

On a side of the outer surface 502 diametrically opposite the protrusions 518, the cap 500 may include one or more ridges or rails 523. Each rail 523 may be substantially linear, and may extend in a longitudinal direction along the outer surface 502. The rails 523 may lift portions of the inner surfaces of the bands 104 off of the outer surface 502, decreasing the frictional force between those portions of the bands 104 and the outer surface 502. This may help position the bands 104 during deployment so that the desired rolling effect can be achieved.

Figure 6A:
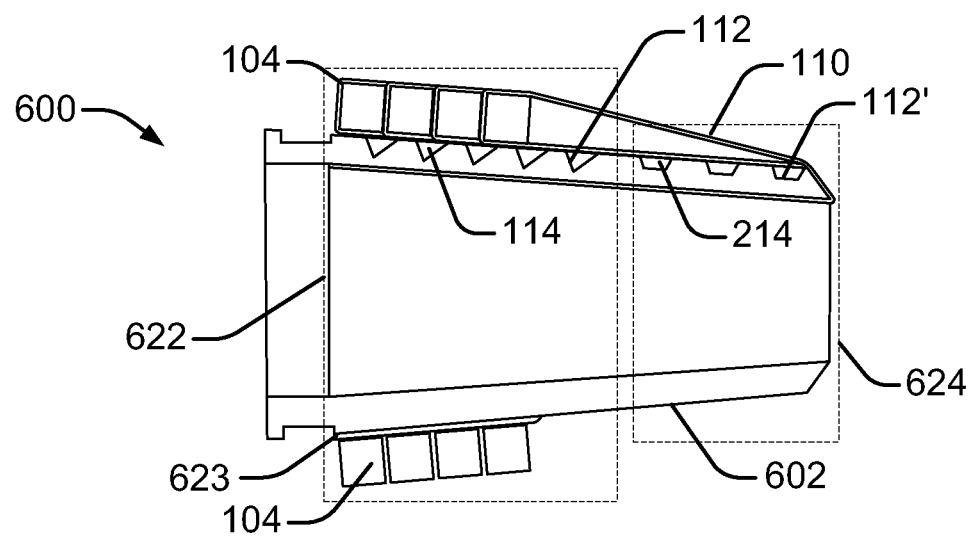
FIGS. 6A and 6B are cross-sectional side views of caps, according to aspects of the present disclosure.
Figure 6B:
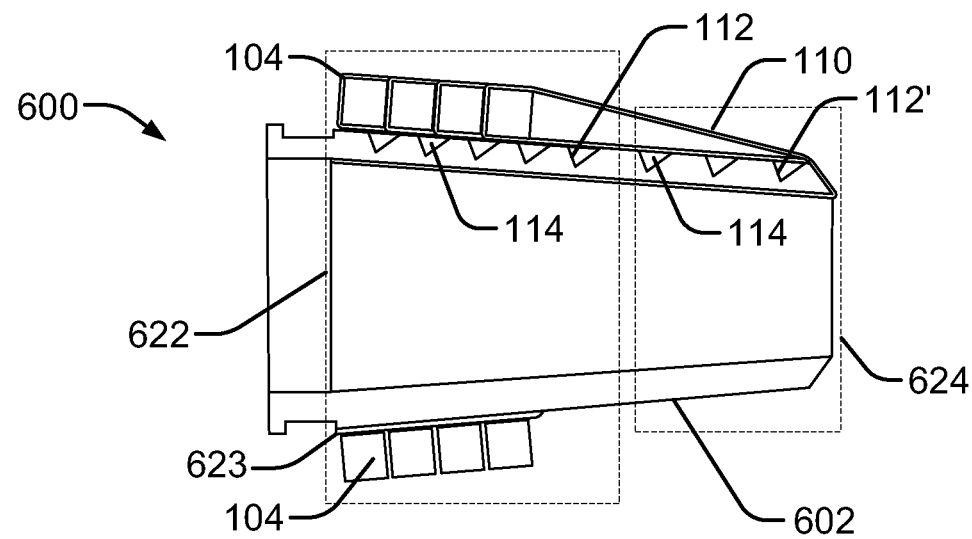

FIGS. 6A and 6B depict a cap 600, where a first region 622 and a second region 624 may include grooves 112' that may have alternative cross-sectional profiles, such as triangular (see FIG. 6B) and trapezoidal (see FIG. 6A). The grooves 112' may provide teetering points for the bands 104, to encourage rolling of the bands 104 as they move distally along the outer surface 602.

Another embodiment of the present disclosure is shown in FIG. 10A. FIG. 10A shows a side perspective view of a cap 1000. The cap 1000 is similar to the cap 500, in that the cap 1000 includes protrusions 518 arranged in columns and/or rows, and grooves 112', similar to the arrangement shown in FIG. 5A. The protrusions 518 may be configured to engage radially inner surfaces of a plurality of bands 104 (FIGS. 5A and 5B), and to initiate rolling of the plurality of bands 104. Alternatively, it is contemplated that bands 104 may be seated, at least partially, in the cavities between protrusions 518. Since only some portions of the bands 104 contact the protrusions 518, surface contact between the bands 104 and the outer surface of the cap 1000 is reduced. Edges of the protrusions 518, such as the proximal and/or distal edges at their peaks, may act as teetering points. When surfaces of the bands 104 engage the teetering points, portions of the bands 104 may teeter, tilt, and rotate into and out of the gaps between the protrusions 518. The reduced surface contact and/or teetering points may encourage rolling of the bands 104 as they move distally along the cap 1000.

The grooves 112' may engage the plurality of bands 104 as they move distally along the cap 1000, and may encourage further rolling of the plurality of bands 104. Edges of the grooves 112', such as their proximal and/or distal edges, may also provide teetering points to cause teetering, tilting, and rotation of bands 104 into and out of the grooves 112', as the bands 104 move along the cap 1000. The cap 1000 may also include a central lumen 1004, a step 1006, and one or more protrusions 1002.

A first plane extending through a center of the distal groove 112', and perpendicular to a longitudinal axis of the cap 1000, may lie approximately 0.350 inches from a parallel second plane extending through a proximal end of the one or more protrusions 1002. A parallel third plane extending through a center of the proximal groove 112', may lie approximately 0.150 inches from the second plane. The spacing between the planes ensures that visualization through the cap 1000, using an imaging device 1007 configured to abut the protrusions 1002, is minimally obstructed. For example, when the imaging device 1007 abuts the protrusions 1002, the imaging device 1007 may be positioned such that the protrusions 518, and/or bands 104 on the protrusions 518, are outside of (e.g., proximal to) a field of view 1009 through a lens 1008 of the imaging device 1007. The protrusions 518 and/or bands 104 thereon may be outside of the field of view 1009 even if portions of the protrusions 518 and/or bands 104 thereon may be distal to the imaging device 1007.

Figure 10B:
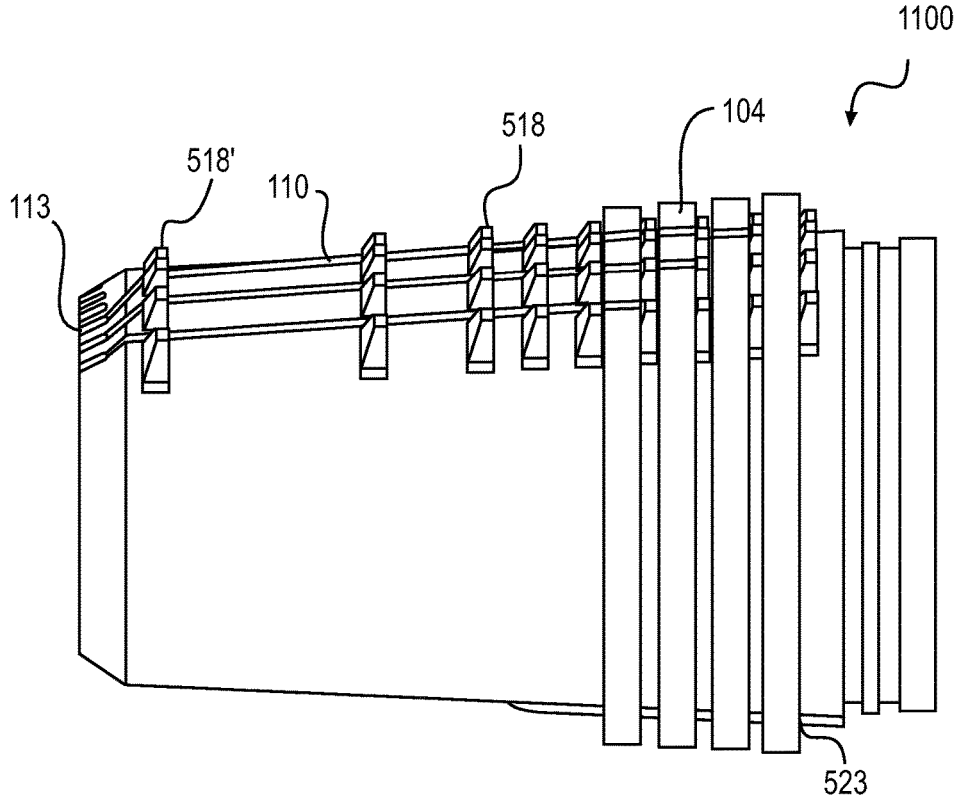

Another embodiment of the present disclosure is shown in FIG. 10B. FIG. 10A shows a side perspective view of a cap 1100. The cap 1100 is similar to the caps 500 and 1000, in that the cap 1100 includes protrusions 518 arranged in columns and/or rows in a manner similar to the arrangements shown in FIGS. 5A and 10A. The cap 1100 differs in that it includes two additional circumferential rows of protrusions 518', similar to rows of protrusions 518, in place of the grooves 112'. The protrusions 518 may initiate rolling of the bands 104, and the protrusions 518' may encourage further rolling of the bands 104. Edges of the protrusions 518', such as the proximal and/or distal edges at their peaks, may provide teetering points for encouraging teetering, tilting, and rotating of the bands 104 into and out of the gaps between the protrusions 518', as they move distally along the cap 1100. The cap 1100 is similar to the cap 1000, in that the cap 1100 may include a central lumen 1004, a step 1006, and one or more protrusions 1002.

A first plane extending through a center of the distal row of protrusions 518', and perpendicular to a longitudinal axis of the cap 1100, may lie approximately 0.350 inches from a parallel second plane extending through a proximal end of the one or more protrusions 1002. A parallel third plane extending through a center of the proximal row of protrusions 518', may lie approximately 0.150 inches from the second plane. The spacing between the planes ensures that visualization through the cap 1100, using an imaging device (not shown) abutting the protrusions 1002, is minimally obstructed.

Figure 10C:
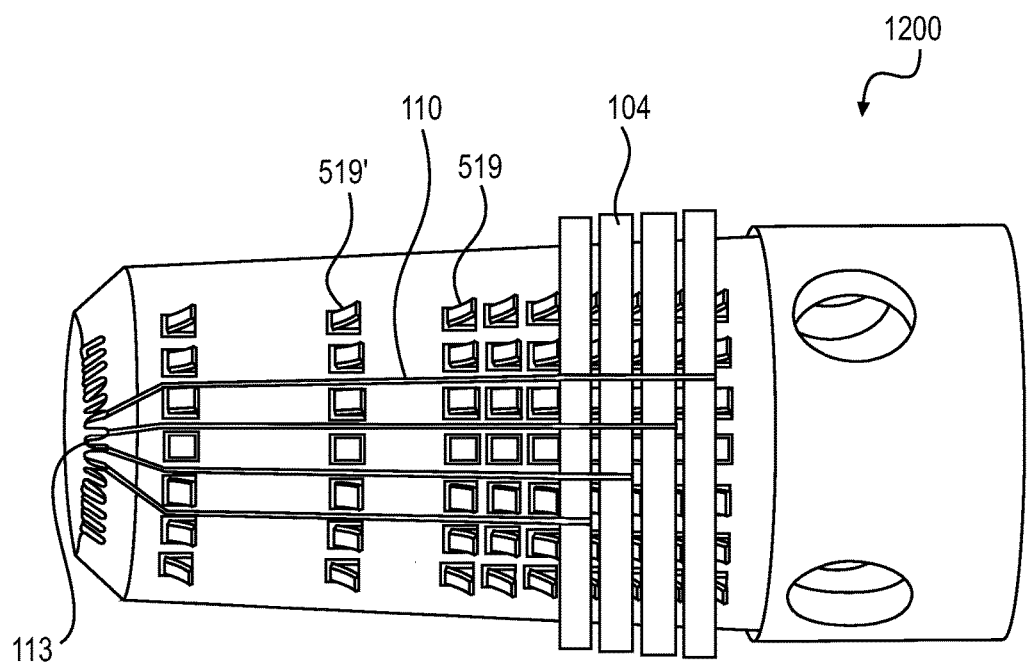

Another embodiment of the present disclosure is shown in FIG. 10C. FIG. 10C shows a top perspective view of a cap 1200. The cap 1200 is similar to the caps 500, 1000, and 1100, in that the cap 1200 includes protrusions 519 arranged in columns and rows, to initiate rolling of the bands 104, in a manner similar to the arrangement of the protrusions 518 shown in FIGS. 5A, 10A, and 10B. The protrusions 519 may reduce surface contact between bands 104 and the outer surface of the cap 1200, and/or provide teetering points at the edges at their peaks, to encourage teetering, tilting, and rotating of portions of bands 104 into and out of gaps between the protrusions 519, thereby encouraging rolling of the bands 104 as they move distally along the cap 1200.

The cap 1200 is similar to the cap 1100, in that the cap 1200 includes two additional circumferential rows of protrusions 519', similar to rows of protrusions 518', in a position analogous to the position occupied by rows 518'. The protrusions 519 may initiate rolling of the bands 104, and the protrusions 519' may encourage further rolling of the bands 104. Radially-inner portions of the bands 104 may be seated in gaps between the protrusion 519'. Alternatively, radially-inner surfaces of the bands 104 may sit on peaks of the protrusions 519', supported, for example, by two or more longitudinally-adjacent peaks.

Edges of the protrusions 519', such as the edges at their peaks, may provide teetering points for encouraging teetering, tilting, and rotating of the bands 104 into and out of the gaps between the protrusions 519', as they move distally along the cap 1200. The cap 1200 is similar to the cap 1000, in that the cap 1200 may include a central lumen 1004, a step 1006, and one or more protrusions 1002. The protrusions 519 and 519' have a triangular or wedge shape, unlike the protrusions 518 and 518', which may have a trapezoidal or pyramidal shape.

It is contemplated that each of the protrusions 518, 518', 519, and 519' may have a width of approximately 0.023 inches and a height of approximately 0.035 inches, a width of approximately 0.028 inches and a height of approximately 0.025 inches, or a width of approximately 0.028 inches and a height of approximately 0.035 inches. Other dimensions may also be used. The exact dimensions used may depend on a number of factors including, for example, the type of band being used.

It is also contemplated that the above-described micropatterns 412 and microstructures 422 may be applied to regions of the outer surface of any of the caps 500, 600, 1000, 1100, or 1200. For example, micropatterns 412 and microstructures 422 to enhance gripping between the outer surface and the bands 104 may be applied to a region of the outer surface distal to the one or more protrusions 1002 that form a stop for the imaging device (not shown), including on any grooves or protrusions in that region of the outer surface.

Figure 7A:
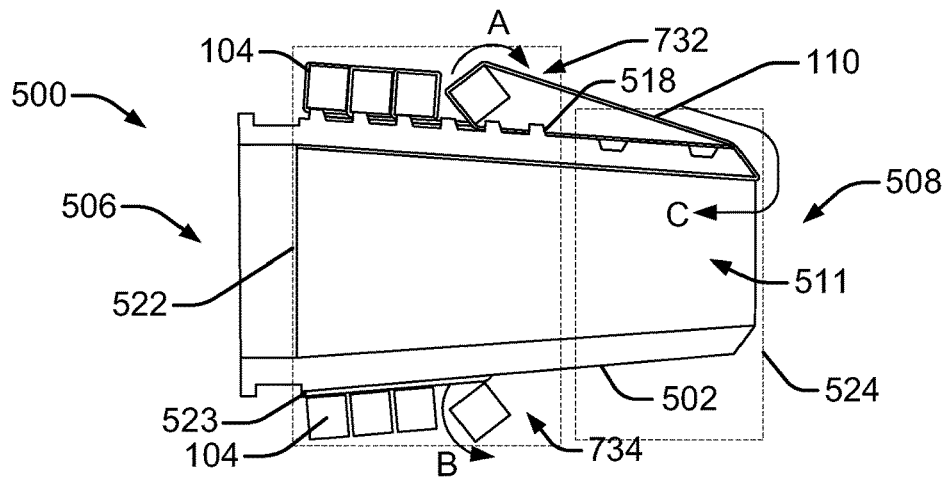
FIGS. 7A-7F are cross-sectional side views of the cap of FIG. 5A, in use, according to aspects of the present disclosure.

The series of FIGS. 7A-7F shows the cap 500 in use. The series may be applicable to any of the other cap embodiments described herein. FIG. 7A shows an exemplary rolling motion of a single band 104 enabled through a pull, depicted through the arrow C, of the suture 110 from a proximal end 806 of an endoscope 802 (see FIG. 8). The endoscope 802 may be the endoscope 150 discussed in connection with FIG. 1A, or may be similar to the endoscope 150. Pulling the suture 110 in the direction of arrow C may initiate distal movement of the band 104. As the band 104 encounters a deployment feature, such as one or more of the protrusions 518, the protrusions 518 force at least a portion of the band 104 to teeter, tilt, and roll, particularly at the section where the suture 110 is wrapped around the band 104. There may be some sliding before or after the roll. This section of the band 104 is referred to as section 732, and the rolling motion is indicated by the arrow A. Another section 734 of the band 104, lying substantially opposite to the section 732, may also roll, or may slide for an extent of travel and roll for another extent of travel. A corresponding rolling motion at the portion 734 is depicted using the arrow B. The rolling of the section 732 may cause portions of the band 104 to twist, leading to rolling of the section 734. Additionally or alternatively, rolling of the section 734 may be initiated or assisted by applying the micropattern 412 to portions of the outer surface 502 that contact the section 734.

The section 732 may be more distal than the section 734, due to the force exerted on the section 732 by the suture 110. Thus, the band 104 may be tilted as it travels distally along the cap 500. This may cause different sections of the band 104 to roll at different times. While some tilting may be desirable, the degree of tilting may be controlled using the rails 523 to reduce frictional contact between the section 734 and the outer surface 502. The degree of tilting may also be controlled by increasing or reducing the gripping force between portions of the band 104 and the outer surface 502, using appropriate micropatterns 412.

Figure 7B:
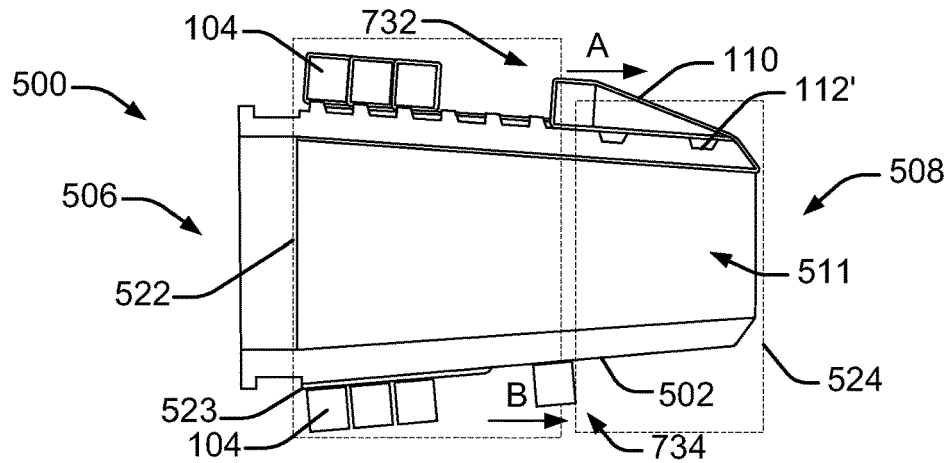

In FIG. 7B, the section 732 of the band 104 is shown to have accomplished at least a first roll, which may be anywhere from a 90° roll to a 360° roll, while the suture 110 continues to pull the band 104 distally through the second region 524. The section 734 may exit the first region 522 and may slide and/or roll towards the second region 524.

Figure 7C:
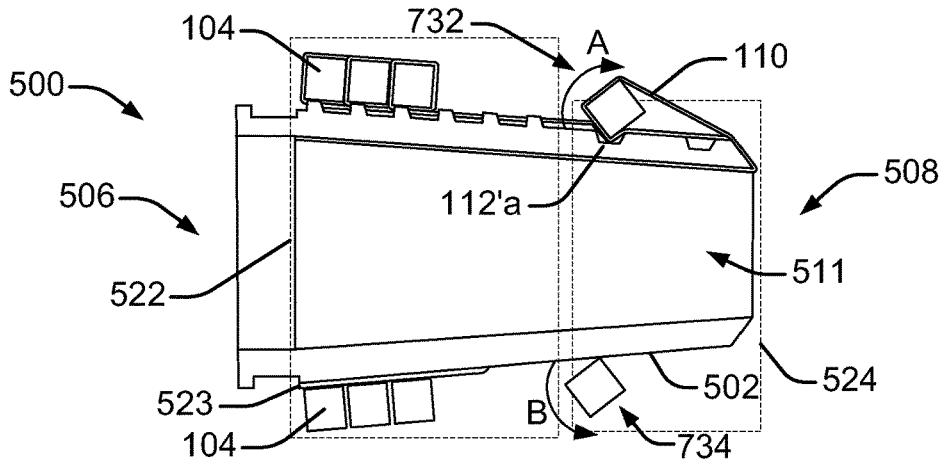
Figure 7D:
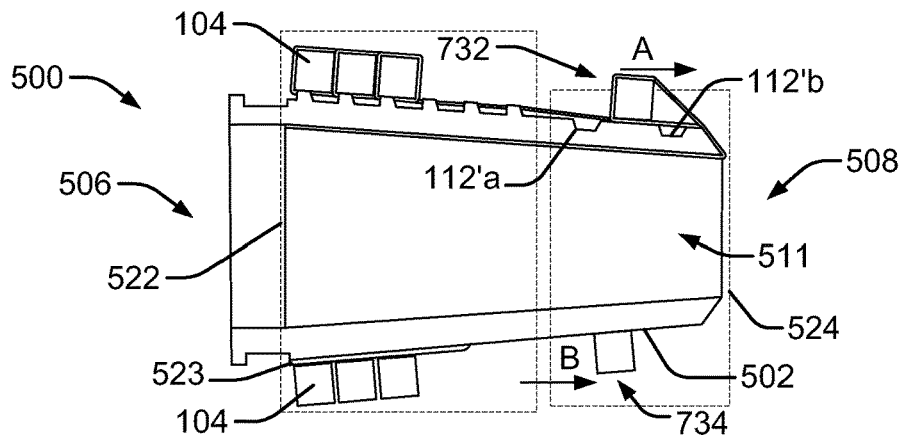
Figure 7E:
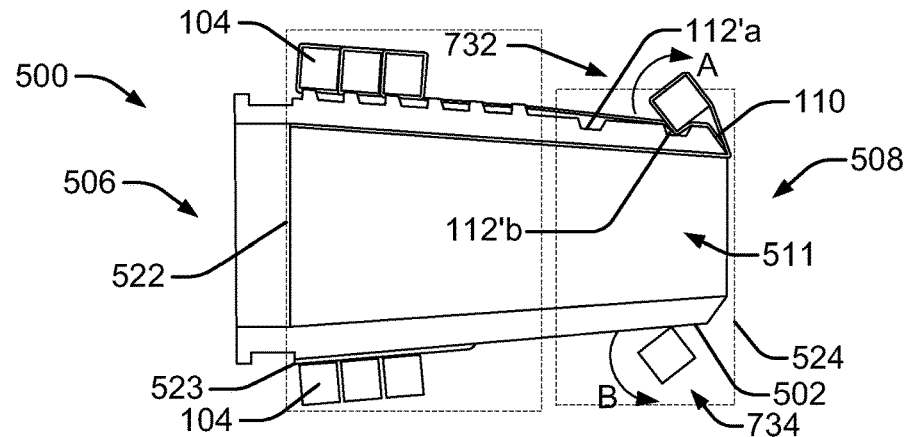
Figure 7F:
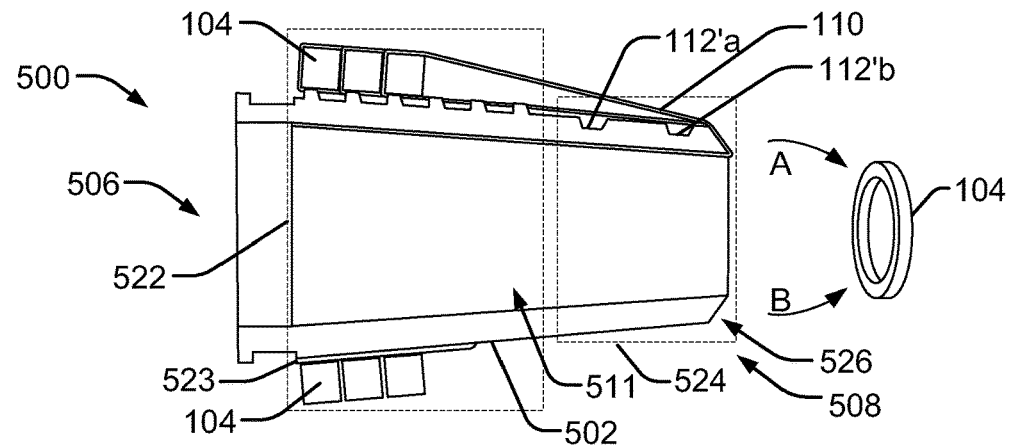

FIG. 7C depicts both the section 732 and the section 734 in the second region 524. Engagement between the section 732 and the groove 112'a may cause the section 732 to teeter, tilt, and roll. Thereafter, in FIG. 7D, as the proximal pulling of the suture 110 continues, the band 104 continues to move distally. In some cases, section 732 may slide for an extent instead of rolling. The same may be true for section 734. When the section 732 reaches the second groove 112'b, the section 732 may teeter, tilt, and roll, and enter at least partially within the second groove 112'b (as shown in FIG. 7E). Rolling of the section 732 may initiate rolling of the section 734.

As the band 104 reaches the distal end portion 508, continued pulling of the suture 110 may deploy the band from the cap 500. The chamfered edge 526 at the distal end portion 508 may facilitate deployment of the band 104 from the distal end portion 508. It is contemplated that by the time the band 104 reaches the distal end portion 508, the sections 732 and 734 may be substantially aligned such that the deploy off the distal end portion 508 substantially simultaneous. Put another way, the tilting of the band 104 due to the section 734 initially lagging behind the section 732, may decrease as the band 104 proceeds distally along the cap 500. Positioning of section 734 relative to section 732 may be adjusted or controlled using, for example, one or more micropatterns 412 to slow down or speed up one section relative to the other.

Figure 8:
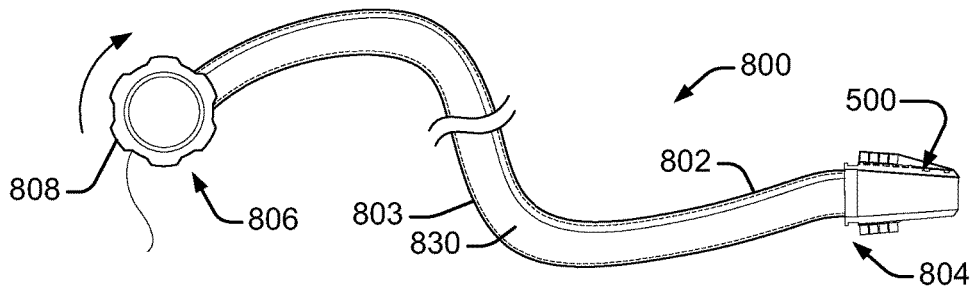
FIG. 8 is a medical device, including a cap, according to aspects of the present disclosure.

FIG. 8 depicts a medical device 800, forming an endoscopic system according to aspects of the present disclosure. The medical device 800 includes a an endoscope 802, an endoscopic shaft 803, a cap, such as the cap 500, secured at the endoscope's distal end 804, and a handle assembly 808 disposed at a proximal end 806. It should be understood that any of the other caps described in this disclosure may be used in place of the cap 500.

The endoscopic shaft 803 may have one or more working channels or lumens, such as a lumen 830, extending through the endoscopic shaft 803. The lumen 830 may carry medical devices such as a vacuum suction mechanism, endoscopic imaging device, light source, snare, and/or any other suitable medical device. The suture 110 may be operatively coupled to a rotary trigger disposed as part of the handle assembly 808, at the proximal end 806 of the medical device 800. The suture 110 may pass through the lumen 830, to the cap 500, and eventually to the bands 104.

Figure 9A:
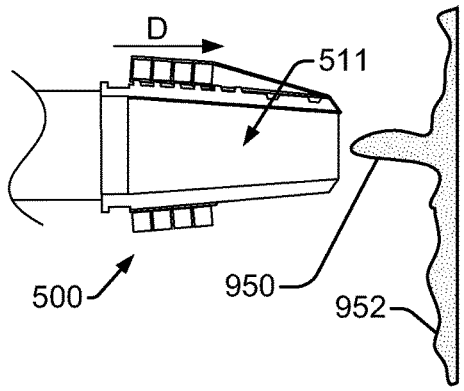
FIGS. 9A-9D are cross-sectional side views showing the medical device of FIG. 8, in use, according to aspects of the present disclosure.
Figure 9B:
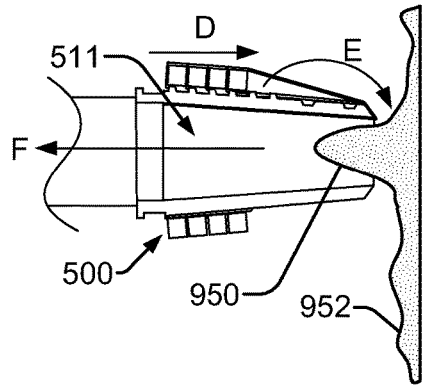

The series of FIGS. 9A to 9D depict an application procedure of the medical device 800, which may be employable with any of the embodiments of the caps discussed in the present disclosure. FIG. 9A depicts the medical device 800, equipped with the cap 500, proceeding towards a target area of tissue 950 on an internal wall 952 of a patient's body. An arrow D depicts the movement of the medical device 800.

Moving further towards the undesired tissue 950, an operator may position the medical device 700 in contact with, and/or at least partially around, the target tissue 950. A suction mechanism (not shown) may generate a vacuum force (arrow F) through the endoscope lumen 830, thus pulling the undesired tissue 950 into the cavity 511. A proximal pull on the suture 110, enabled through the handle assembly 808, may enable the band 104 to be released around the target tissue 950 (along the path of arrow E), ligating the target tissue 950. The release of the band 104 may occur in the manner discussed in connection with the series of FIGS. 7A to 7F.

Figure 9C:
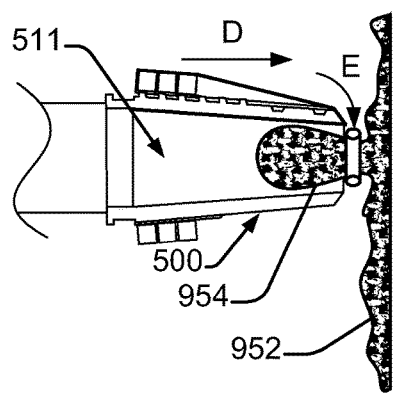
Figure 9D:
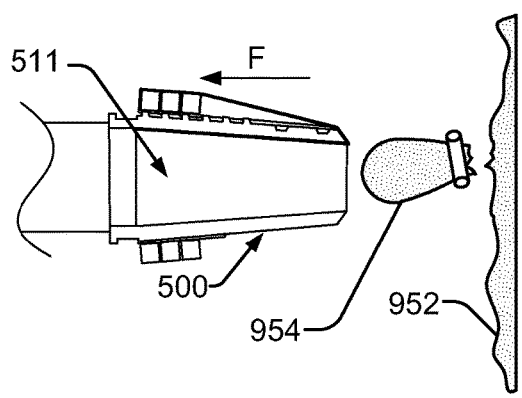

Subsequently, once the band 104 is released over the target tissue 950, a ligated tissue or pseudo polyp 954 is obtained, as shown in FIG. 9C. Thereafter, a tissue resection device, such as a snare, may be brought forth from within the lumen 830 or outside of the endoscope 800, for carrying out a tissue resection operation (such as an EMR) on the newly formed ligated tissue 954.

Embodiments of the present disclosure may be used in any medical or non-medical environment. In addition, at least certain aspects of the aforementioned embodiments may be combined with other aspects of the embodiments, or removed, without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the disclosure being indicated by the following claims.

What is claimed is:

1. A medical device for deploying a ligation band, comprising:
   a tubular body including:
   a proximal end,
   a distal end,
   a radially inner surface defining a lumen through the tubular body, and a radially outer surface including:
a plurality of first protrusions arranged in circumferential rows extending transverse to a longitudinal axis of the body at least partially around a proximal region of the radially outer surface, wherein adjacent rows of the first protrusions are separated from one another in a proximal to distal direction by a first distance, and
a plurality of grooves, each groove extending at least partially around a distal region of the radially outer surface, all of the grooves being distal of a distal-most row of the first protrusions, wherein adjacent grooves are separated from one another in a proximal to distal direction by a second distance larger than the first distance.

2. The medical device of claim 1, wherein the first protrusions and grooves are configured to engage the ligation band during movement of the ligation band along the radially outer surface.

3. The medical device of claim 1, wherein the radially inner surface includes at least one radially inwardly extending second protrusion configured to engage an imaging device.

4. The medical device of claim 3, wherein all of the grooves are distal to the second protrusion.

5. The medical device of claim 3, wherein the imaging device includes a lens, the imaging device having a field of view through the lens, wherein the second protrusion is configured to engage the imaging device to position the imaging device so the first protrusions are outside of the field of view of the imaging device.

6. The medical device of claim 1, wherein the radially outer surface includes at least one micropattern formed by a plurality of microstructures.

7. The medical device of claim 1, wherein the first protrusions and grooves reduce surface contact between the ligation band and the radially outer surface, and include teetering points for initiating tilting of the ligation band as the ligation band moves across the first protrusions and the grooves.

8. A medical device for deploying a ligation band, comprising:
a tubular body including:
a proximal end,
a distal end,
a radially inner surface defining a lumen through the tubular body, the radially inner surface including at least one radially inwardly extending first protrusion configured to engage an imaging device, wherein a proximal region of the tubular body is proximal to the first protrusion, and a distal region of the tubular body is distal to the first protrusion, and
a radially outer surface including:
a plurality of second protrusions arranged in circumferentially extending rows on the radially outer surface, in the proximal region of the tubular body, wherein adjacent rows of the second protrusions are separated from one another in a proximal to distal direction by a first distance, and
a plurality of grooves, each groove extending circumferentially into the radially outer surface, the grooves being distal of a distal-most row of the second protrusions, wherein adjacent grooves are separated from one another by a second distance larger than the first distance.

9. The medical device of claim 8, wherein the grooves are configured to engage the ligation band during movement of the ligation band along the radially outer surface.

10. The medical device of claim 8, wherein the radially outer surface includes at least one micropattern formed by a plurality of microstructures.

11. The medical device of claim 10, wherein the at least one micropattern increases a hydrophobicity of the radially outer surface in the distal region of the tubular body.

12. The medical device of claim 8, wherein the second protrusions reduce surface contact between the ligation band and the radially outer surface, and include teetering points for initiating tilting of the ligation band as the ligation band moves across the second protrusions.

13. A medical device for deploying a ligation band, comprising:
a tubular body including:
a proximal end,
a distal end,
a radially inner surface defining a lumen through the tubular body, and
a radially outer surface including:
a distal region,
a proximal region, and
a plurality of radially inwardly extending grooves formed in the radially outer surface, in the distal region, each groove extending transverse to a longitudinal axis of the body,
a plurality of protrusions arranged in circumferential rows in the proximal region, the protrusions being positioned on the proximal region proximally of a proximal-most one of the grooves.

14. The medical device of claim 13, wherein each of the plurality of radially inwardly extending grooves extends circumferentially around a portion of the radially outer surface.

15. The medical device of claim 13, wherein each of the plurality of radially inwardly extending grooves includes a middle portion and opposite end portions, the middle portion being at least one of wider than and deeper than the opposite end portions.

16. The medical device of claim 13, wherein each of the plurality of radially inwardly extending grooves includes a proximal surface and a distal surface, a length of the proximal surface being shorter than a length of the distal surface.

17. The medical device of claim 13, wherein at least one of the radially inwardly extending grooves includes an edge, the edge acting as a teetering point for initiating tilting of the ligation band as the ligation band moves over the edge.

* * * * *